United States Patent [19]
Zelmanovic et al.

[11] Patent Number: 6,074,879
[45] Date of Patent: Jun. 13, 2000

[54] SYNTHETIC POLYMER PARTICLES FOR USE AS STANDARDS AND CALIBRATORS IN FLOW CYTOMETRY

[75] Inventors: David Zelmanovic, Monsey; William Moskalski, Elmsford, both of N.Y.; Ronny DeClercq, Aalter; Frank Louwet, Diepenbeek, both of Belgium; Eberhard Kuckert, Leverkusen; Wolfgang Podszun, Cologne, both of Germany

[73] Assignee: Bayer Corporation, Tarrytown, N.Y.

[21] Appl. No.: 09/099,233

[22] Filed: Jun. 17, 1998

Related U.S. Application Data

[60] Provisional application No. 60/050,477, Jun. 23, 1997.

[51] Int. Cl.[7] .................................................. G01N 31/00
[52] U.S. Cl. .................................. 436/10; 436/8; 436/63; 436/164; 436/166; 436/172; 702/19; 702/21
[58] Field of Search ................................ 436/8, 10, 16, 436/63, 164, 166, 172; 702/19, 21

[56] References Cited

U.S. PATENT DOCUMENTS

| | | | |
|---|---|---|---|
| 4,331,862 | 5/1982 | Ryan | 377/29 |
| 4,489,162 | 12/1984 | Hawkins et al. | 436/10 |
| 4,704,891 | 11/1987 | Recktenwald et al. | 250/252.1 |
| 4,735,504 | 4/1988 | Tycko | 356/336 |
| 4,767,206 | 8/1988 | Schwartz | 356/73 |
| 4,777,139 | 10/1988 | Wong et al. | 436/18 |
| 4,857,451 | 8/1989 | Schwartz | 436/10 X |
| 4,867,908 | 9/1989 | Recktenwald et al. | 436/10 X |
| 4,868,126 | 9/1989 | Schwartz | 436/10 |
| 5,073,497 | 12/1991 | Schwartz | 436/8 |
| 5,084,394 | 1/1992 | Vogt et al. | 436/8 |
| 5,093,234 | 3/1992 | Schwartz | 435/7.21 |
| 5,093,445 | 3/1992 | Podszun et al. | 526/243 |
| 5,270,354 | 12/1993 | Vermeersch et al. | 523/334 |
| 5,380,663 | 1/1995 | Schwartz et al. | 436/10 |
| 5,540,494 | 7/1996 | Purvis, Jr. et al. | 356/73 |
| 5,837,547 | 11/1998 | Schwartz | 436/10 |

FOREIGN PATENT DOCUMENTS

| | | |
|---|---|---|
| 0 399 729 A2 | 11/1990 | European Pat. Off. |
| 0 652 428 A1 | 5/1995 | European Pat. Off. |

*Primary Examiner*—Maureen M. Wallenhorst
*Attorney, Agent, or Firm*—Morgan & Finnegan, LLP

[57] ABSTRACT

The invention describes novel methods for calibrating or standardizing flow cytometry instruments using synthetic polymer particles or beads having physical properties which provide advantages for their use in such instruments. The polymer particles or beads employed in the calibration methods are spherical, have an average particle diameter of from about 1 to about 8 microns, a relatively narrow particle distribution, and a low refractive index, i.e., from about 1.35 to about 1.45. The particles are safe, stable for long time periods and are particularly suitable for employment as hematology analyzer calibration substances. The invention provides an advantageous improvement over the types of standards currently used to calibrate a variety of instruments that rely on light scatter combined with other parameters to identify and measure biological particles or cells, as well as nonbiological particles. In particular, using the calibration/ standardization method and polymer particles according to the present invention allows hematology instruments to be calibrated and standardized for subsequent accurate and reliable determinations of red blood cells, reticulocytes, white blood cells and platelets in whole blood samples.

28 Claims, 2 Drawing Sheets

RBC 4.93 x 10⁶/μL
MCV 60.7 fl
CHCM 36.9 g/dl
RDW 11.8%
HDW 1.57 g/dl

MeanX 19.5
Sigmax 2.9
MeanY 20.0
Sigmay 3.1

SYNTHETIC POLYMER PARTICLES FOR USE AS STANDARDS AND CALIBRATORS IN FLOW CYTOMETRY

This application claims the benefit of U.S. Provisional Application No. 60/050,477, filed Jun. 23, 1997.

FIELD OF THE INVENTION

The present invention relates to products and methods used in flow cytometry instrumentation for the analysis of biological particles or cells. More particularly, the invention relates to synthetic polymer materials and methods for standardizing or calibrating flow cytometry instruments prior to using the instruments for analyzing such particles, for example, the cellular components of whole blood.

BACKGROUND OF THE INVENTION

The analysis of particles, particularly biological particles, and cells is routinely performed using a variety of commercially-available instruments which determine the characteristics of such particles based on one or more light-related signals which pass through the instrument. Flow cytometers allow the determination of the characteristics of particles using techniques in which the particles are moving in a liquid stream or carried in a suspension. Typically, in flow cytometry instruments, cells or other biological particles flow in a liquid stream so that each particle, virtually one cell at a time, passes through a sensing region that is capable of measuring the physical or chemical characteristics of the particles.

A variety of signals associated with different characteristics of the particles under analysis may be detected. Such signals include electrical, acoustical, optical and radioactive. Flow cytometers generally rely on optical signals for the analysis of particles which pass through the instrument. Whether or not an instrument analyzes particles in a static or a dynamic state, those skilled in the art will appreciate that calibration and standardization are required prior to performing particle analyses. Under normal circumstances, calibration occurs as one or more preliminary presteps in preparing instruments for proper use and measurement and to ensure accurate and reliable assay results. This is especially important since cells, or other biological particles, are extremely small and the signals to be detected, in relation to the size of the cells or particles, are often at a low magnitude.

Flow cytometers and other biological particle and cell analysis instruments are commonly calibrated with particles which simulate or approximate the types of particles or cells that are intended to undergo analysis. Thus, calibration particles should be selected or designed so that they have characteristics and parameters that are quite similar to those of the particles or cells to be tested in the instruments. Exemplary characteristics and parameters include similarities in size, volume, surface characteristics, granularity properties, and, if necessary, color features, such as stains, dyes, immunofluorescent tags, and the like. Accordingly, it is to be understood that the particles to be analyzed after calibration or standardization of an analyzer need not be restricted biological cells. For example, particles to be assayed may be found in oil-in-water suspensions, milk, or another nonbiological medium.

Hematology analyzers represent but one specific type of instrumentation designed and employed for the determination and measurement of the characteristics of cells and biological particles in whole blood. As a particular, yet nonlimiting, example, hematology systems commercially available from Bayer Corporation optically analyze, determine the characteristics of and measure erythrocytes (red blood cells), reticulocytes (immature red blood cells), leukocytes (white blood cells) and platelets in whole blood samples.

Past and present calibration procedures for flow cytometry instruments, including hematology analyzers, involve the use of fixed and/or sphered red blood cells, for example, human and chicken red blood cells, for the calibration steps and for standardizing optical signals such as light scattering. See, for example, U.S. Pat. No. 4,489,162 to Hawkins et al. and U.S. Pat. No. 4,777,139 to S.-C. Wong et al. While the use of red blood cells procured from mammals and humans may be reliable in some aspects of calibration procedures, there are drawbacks to the use of these types of "natural" calibrator cells. For example, the preparation of sphered and fixed red blood cells entails the blood-drawing process and other blood manipulations which involve contact with potentially biohazardous material. Further, because the stability of red cells as optical standards is limited, i.e., about six months, the cell standards must be reproduced periodically, typically, two or more times a year.

In addition to biological samples for calibration and standardization purposes, microspheres or microbeads have also been used for calibrating cellular analysis instruments. For example, U.S. Pat. No. 4,331,862 to W. L. Ryan describes beads composed of latex material for calibrating a particle counting instrument. Plastic microbeads are disclosed for calibrating flow cytometers and cell analysis instruments in U.S. Pat. No. 4,704,891 to D. J. Recktenwald et al. Calibration beads for calibrating flow cytometry instruments are commercially available from the Flow Cytometry Standards Corporation, Research Triangle Park, N.C. In general, such microsphere beads are not produced with a consideration for the proper refractive index values of actual cells and biological particles.

Nonbiological bead polymers having an average particle diameter of from 0.5 to 10 μm and containing 1% to 60% of chemically bound fluorine are disclosed in U.S. Pat. No. 5,093,445 to W. Podszun et al. for use as matting agents and spacers in photographic recording materials. This patent does not relate to particle calibrators for flow cytometry and does not recognize refractive index as a critical parameter for such use. Indeed, the present inventors have determined that the polymer beads exemplified in this patent have refractive indices which are significantly higher than 1.45, which is considered to be at or near the upper limit of refractive index, particularly as it relates to blood cells, as described further hereinbelow.

Other types of flow cytometry instruments, such as fluorescence flow cytometers, use polymer beads made of materials such as polystyrene to standardize the optical signals. The signals typically include forward scatter (0–2 degrees), side scatter (90 degrees) and fluorescence intensity. The polymer bead materials, although safe and stable for about five years or more, are particularly unsatisfactory for light scattering flow cytometry instruments. More particularly, for particles of a given volume, currently-available polymer beads produce scattering signals that are different from those of red blood cells of the same volume, even if the red blood cells are sphered. This is because the refractive index (r.i.) of a polymeric material such as polystyrene is quite different from that of red blood cells. While the r.i. of polystyrene is high, i.e., about 1.59, the r.i. of a red blood cell is about 1.40–1.42. It is well known from the Mie Scattering Theory that the light scattering properties of small spheres are significantly influenced by their r.i. values. Thus, the scattering patterns of polymer beads currently used in flow cytometry instruments are not truly representative of the scattering patterns of actual red blood cells. Consequently, the forward and side scatter signals do not provide important information, such as cell size and refractive index, which are related to cell density and activation state.

In addition, platelet light scattering signals are currently standardized using either sphered and fixed red blood cells in the case of some types of analyzers, for example, commercial hematology analyzers, or using appropriately-sized polymer beads in the case of fluorescence flow cytometers. However, the scattering signals of platelets are typically much smaller than those of red blood cell (i.e., by more than a factor of 10). Also, the refractive index of platelets is only about 1.35 to about 1.40. Accordingly, the present invention advantageously provides a material with the light scattering properties associated with actual platelets, as well as with the stability and safety of non-biological polymeric materials for flow cytometry analyses.

Moreover, white blood cell light scattering signals are currently standardized using either sphered and fixed red blood cells or polymer beads. White blood cell scattering signals are typically larger than those of red blood cells and their refractive indices are lower, typically about 1.37 to about 1.40. Accordingly, the present invention advantageously also provides a material with the light scattering properties associated with actual white blood cells, as well as with the stability and safety of non-biological polymeric materials for flow cytometry analyses.

As a further particular example, some commercial hematology analyzers enumerate reticulocytes (immature red blood cells) based on a combination of their light scattering properties and their ability to bind to cationic dyes, such as Oxazine 750, and thus absorb light at the absorption wavelength of the dyes. Currently, the absorption channel is standardized using fixed and sphered red blood cells that do not contain dye. The standardization relies on the light scattered outside the collection cone-angle of the absorption detector to provide a "pseudo-absorption" signal which mimics true light absorption. However, this method is not optimal, since the pseudo-absorption signal is significantly less than the true absorption signal produced by many reticulocytes. Thus, the optical standard used does not best represent true signals encountered in practice. Appropriately-colored polymeric beads made of materials such as polystyrene are also not useful for this purpose, since their high r.i. values result in scattering signals that are outside the scattering signal detector ranges. Therefore, for standardizing light scattering and absorption measurements of reticulocytes, it is desirable to produce a material that has the light scattering (and absorption) properties of reticulocytes and that is also safe and stable. In the case of fluorescence flow cytometry in which the combination of scattering and fluorescence properties is used to analyze blood cells, it is desirable to produce a material having the light scattering and fluorescence properties of the particular cells being analyzed, and having the safety and stability of non-biological polymeric materials.

Thus, there is a present need and a desire for standardization and calibration materials and procedures that provide accurate and reproducible results in the determination of the characteristics of both nonbiological and biological particles and cells, in a variety of analysis instruments, including hematology analyzers. There is also a current need for the production of safe and stable calibration particles for standardizing flow cytometry instruments. Such particles optimally need to have a long shelf-life and to have properties, such as particle size and refractive index, that are virtually identical to those of the natural particles and cells which they represent during the calibration/standardization process.

In addition, for hematology analyses, there is a need for the development of non-biological polymeric particles for standardizing flow cytometers wherein the standardizing polymer particles employed accurately portray all of the necessary parameters of the respective component blood cells to be analyzed following instrument calibration/standardization. The present invention is directed to the advantageous fulfillment of these current needs and goals in the art.

SUMMARY OF THE INVENTION

Accordingly, it is an object of the present invention to provide novel synthetic polymer particles for use in calibrating or standardizing a flow cytometer, particularly a hematology analyzer, prior to the analysis of nonbiological particles, or biological particles or cells, in which the calibrator/standardizing particles have virtually all of the optical and physical properties of actual particles or blood cells, e.g., authentic red blood cells, reticulocytes, platelets and/or white blood cells, to be analyzed, and the stability and safety of nonbiological polymeric materials.

In accordance with the present invention, the novel calibration particles are designed to have a narrow average particle diameter distribution, a well-defined average particle diameter and a well-defined refractive index value that are virtually identical to those of the authentic particles in various media, or cell types in a biological sample, such as a blood sample, which are to be analyzed.

Another object of the present invention is to provide novel reagents and methods for calibrating or standardizing a flow cytometry instrument prior to the analysis of biological particles or cells, particularly with regard to the analysis of the component cells in a whole blood sample.

Another object and advantage of the present invention is to provide calibration methods and materials that are substantial improvements over those that are known and used in the art. The invention provides the ability for those in the art to calibrate a particle analysis instrument by employing and relying on calibration standards (and/or thresholds) that have been predetermined and are easily manipulated and made available to the user. Using the standards and methods of the present invention during the standardization and calibration procedures of flow cytometry instruments allows for proper standardization and calibration of an instrument, proper alignment of the optical components of the instrument, and optimization of the performance of the instrument for subsequent particle and cell analysis, including the determination of cell size and refractive index from forward and side scatter measurements.

It is yet another object of the present invention to provide calibration/standardization methods and synthetic particles for use in several different particle analysis and detection systems that are based on a combination of light scatter as one measured parameter and the measurement of another known parameter, such as light scatter (i.e., scatter-scatter detection), electrical impedance (i.e., scatter-impedance detection), radio frequency (i.e., scatter-RF detection) and the like. It is to be further understood that the present invention and the advantages and features attendant thereto also may be utilized in other flow cytometry analysis instruments such as fluorescence cell sorters, and may extend to instruments such as image analyzers, automated microscopes, quantitative microscopes, fluorescence microscopes and the like. The materials and techniques of the present invention provide quality assurance for a variety of applications, including medical and clinical diagnostic applications for identifying and determining both normal and abnormal conditions.

Further objects and advantages afforded by the invention will be apparent from the detailed description hereinbelow.

BRIEF DESCRIPTION OF THE FIGURES

FIG. 1A presents the numerical frequency distribution for particles prepared as described in Example 1. In FIG. 1A, the X-axis represents the particle diameter in microns and the Y-axis represents the relative particle count. FIG. 1B presents the volume frequency distribution for the same particles as those of FIG. 1A. In FIG. 1B, the X-axis represents the particle diameter in microns and the Y-axis represents the relative volume occupied by the particles.

DETAILED DESCRIPTION OF THE INVENTION

Figure 1A:
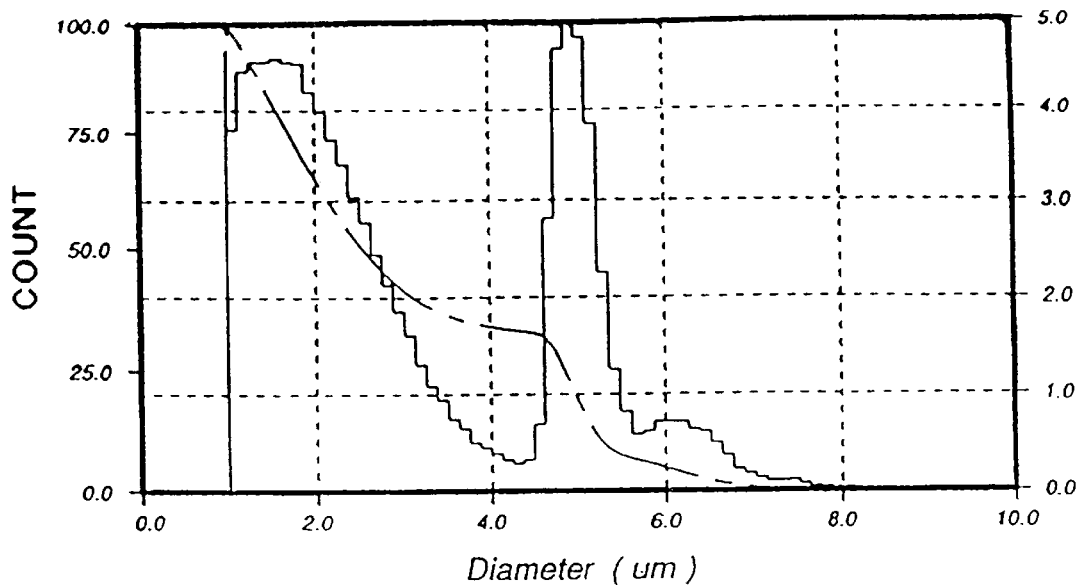
FIGS. 1A and 1B show the determination of the particle count and relative volume of the standardization/calibration synthetic polymer particles according to the present invention, based on an aperture impedance counter (Example 3).

The present invention provides synthetic polymer particles (also referred to as beads or particle beads herein) for employment in a method of calibrating or standardizing flow cytometry instruments for the analysis of biological particles or cells. The polymer particles of the present invention are designed to have properties and parameters that allow them to accurately standardize and calibrate instruments useful for biological particle and cellular analysis prior to carrying out assays on the actual biological particles or cells themselves. The polymer particles of the present invention can also be used to accurately standardize and calibrate instruments useful for the analysis of nonbiological particles in nonbiological media, such as milk or oil-in-water suspensions, prior to performing analyses on the particles.

The present invention is particularly related to synthetic particles for the calibration or standardization of hematology analyzers for analysis of the cellular components of whole blood samples. In accordance with the present invention, for a given cell type, particularly blood cells, the size, shape, volume and refractive indices of the standardizing or calibrator particles are created to be highly reproducible of these same parameters of the actual cells to be assayed. Until the present invention, such particles were neither contemplated nor specifically designed for use as calibrator/standardization materials in the art of flow cytometry and/or hematology analysis.

More particularly, the polymer particles of the present invention are substantially spherical beads and comprise the halide fluorine. The particles have a well-defined average particle diameter (particle size diameter), i.e., mass average, of about 1 μm to about 10 μm, preferably, about 1 μm to about 8 μm, more preferably, about 4 μm to about 6 μm. Preferable average particle diameters for the synthetic polymer particles of the present invention as standardization/calibration materials for particular blood cell types are as follows: about 5.5 μm for red blood cells; about 2.5 μm for platelets; about 8.0 μm for neutrophils; about 7.2 μm for lymphocytes; about 9.0 μm for monocytes; about 8.5 μm for eosinophils and about 7.4 μm for basophils, with a particle size distribution of about +/−0.25 μm, more preferably, about +/−0.1 μm for each of these cell types. In general, the particle size distribution width of the standardization/calibration synthetic particles is about 1% to about 5%. Particle size distribution width is here defined as one standard deviation of the distribution of particle diameters divided by the mean diameter.

In addition, the spherical polymer particles of the present invention have a refractive index generally of from about 1.35 to about 1.45, preferably about 1.35 to about 1.42. Preferable refractive indices for the synthetic polymer particles of the present invention as standardization/calibration materials for particular blood cell types are as follows: about 1.410 for red blood cells; about 1.380 for platelets; about 1.395 for neutrophils; about 1.385 for lymphocytes; about 1.375 for monocytes; about 1.395 for eosinophils and about 1.385 for basophils, with a range of about +/−0.01, more preferably, about +/−0.005 for each of these cell types. In accordance with the present invention, particles comprising fluorine provide optimum low refractive index values for use as standardization/calibration materials. As a particular, non-limiting example, particles that are optimum for use in standardizing and calibrating hematology analyzers for red blood cell analysis in accordance with the present invention have a particle size diameter of about 5 to about 5.5 +/−0.1 μm and a refractive index of about 1.41+/−0.005.

The monodispersity of the polymer calibration particles of the present invention is at least about 65%, preferably at least about 75% and more preferably at least about 85%. Monodispersity as used herein refers to the percentage of polymer particles whose average particle diameter is in the range of the average particle diameter ±33%, by weight, and is achieved by the polymerization process used to produce the particles. Further improvements or refinements of the monodispersity property, for example, to narrow the particle size diameter distribution, can be achieved by the application of physical purification procedures, such as sieving or ultracentrifugation, during the preparation of the particles.

In one embodiment involving the analysis of erythrocytes using flow cytometry, spherical bead polymer particles are prepared having an average particle diameter of about 5.5 μm and a refractive index of 1.4 in accordance with the present invention. Such calibrating substances achieve optimum standardization and calibration of the analyzer instrument for accurate and reliable red blood cell determinations. Other embodiments of the present invention encompass the synthesis and use of spherical bead polymer particles as standardizing and calibrating materials for reticulocytes, white blood cells and platelets. For the analysis of reticulocytes using flow cytometry, the polymer beads are prepared to have an average particle diameter of about 5.5 μm and a refractive index of about 1.410. For the analysis of white blood cells using flow cytometry, the polymer beads are prepared to have average particle diameters as described hereinabove. For the analysis of platelets using flow cytometry, the polymer beads are prepared to have an average particle diameter of about 2.5 μm and a refractive index of about 1.380.

Suitable polymer particles of the present invention comprise polymerized monomeric units such as is shown in the following general formula I:

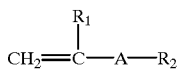

wherein, $R_1$ is hydrogen (H) or methyl ($CH_3$); A is —O—;

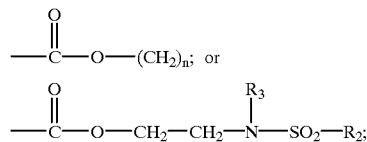

wherein n is 1–5, preferably 1–3; and wherein $R_2$ is a fluorine-containing (F-containing) alkyl group of 1 to 12 carbon atoms. F-containing alkyl groups include perfluoralkyls and partially fluorinated alkyls. $R_3$ is hydrogen (H) or $C_1$–$C_6$ alkyl. As will be appreciated by those skilled in the art, perfluoroalkyls are alkyl groups in which all of the hydrogen atoms are substituted with fluorine.

Preferred are spherical particles or beads comprising polymerized monomer units having the formula:

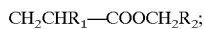

wherein $R_1$ and $R_2$ are as described directly above. The present invention is also intended to encompass particles having polymerized monomer units of the formulae: $CH_2=CR_1COOR_2$ or $CH_2=CHCH_2COR_2$, wherein $R_1$ and $R_2$ are also as described above.

Monomers of the above-described formulae that are suitable for synthesizing the polymeric particles for calibration/standardization of flow cytometry instruments in accordance with the present invention include, but are not limited to, 2-fluorethylacrylate, 2,2,2-trifluoroethylacrylate, 2,2,3,3-tetrafluoropropylacrylate, 2,2,3,4,4,4-hexafluorobutylacrylate, 1H,1H-heptafluorobutylacrylate, 1H,1H,5H-octafluoropentylacrylate, 1H,1H-pentadecafluoroctylacrylate, 2-fluoroethylmethacrylate, 2,2,2-trifluoroethylmethacrylate, 2,2,3,3,3-pentafluoropropylmethacrylate, 1H,1H-hepatafluorobutylmethacrylate, 2,2,3,4,4,4-hexafluorobutylmethacrylate, 1H,1H,5H-octafluoropentylmethacrylate and 1H,1H,11H-eicosafluoroundecylmethacrylate. A preferred polymer particle according to the present invention comprises a homopolymer of 2,2,2-trifluoroethylmethacrylate.

The synthetic polymeric particles may also contain mixtures or combinations of the monomer units.

The polymers comprising the polymerized units of formula I preferably contain fluorine in an amount of from about 22% to about 65%, by weight, based on the total weight of the polymer and, preferably, about 30% to about 55%, by weight, based on the total weight of the polymer. The particles can comprise a single fluorine-substituted monomer or mixtures of two or more fluorine-substituted monomers.

In addition to the above-described fluorine-containing monomers, the synthetic polymer particles for use according to the present invention can contain up to about 50%, by weight, of other copolymerized monomers, for example, styrene, α-methylstyrene, vinyltoluene, vinylbenzylchloride, butadiene, isobutylene, acrylic acid esters, such as ethylacrylate, n-butylacrylate, ethylhexylacrylate, methylmethacrylate, ethylmethacrylate, iso-butylmethacrylate, ethylhexylmethacrylate, decylmethacrylate and dodecylmethacrylate. Preferred is methylmethacrylate. Moreover, if copolymers are used in addition to the fluorine-containing monomers, comonomers that are free of fluorine or that contain other halides are suitable.

The spherical polymer particles for use as calibration/standardization materials are produced by polymerizing at least one monomer of formula I optionally together with at least one other monoethylenic unsaturated compound. The monomers are polymerized in a polar medium comprising a solvent for the above-described monomer(s) and a precipitation compound for the resulting polymer particle, in the presence of a high molecular weight dispersing agent and a radical former as initiator. In general, the polymer particles can be synthesized as described in U.S. Pat. No. 5,093,445.

Illustrative polar media suitable for use include solvents such as dioxane, acetone, acetonitrile, dimethylformamide and alcohols. Lower alcohols, i.e., having from 1 to 4 carbon atoms, are preferred, in particular, methanol, ethanol, n-propanol, isopropanol, n-butanol, isobutanol and tert-butanol. Mixtures of different solvents are also suitable; mixtures of different alcohols are preferred. Preferably, a solvent and water mixture is used. In such alcohol/solvent mixtures, the alcohols can contain up to about 25% by weight of water.

When the polar medium contains water, sodium per ox Qdisulfate ($Na_2S_2O_8$) may also be suitable for inclusion in the preparation scheme. In general, the radical form is added in an amount of from about 0.05% to about 10% by weight, preferably about 0.2% to about 5% by weight, based on the total weight of the monomer or monomer mixture.

The high molecular weight dispersing agents used for preparing the particles may be natural or synthetic macromolecular compounds which are soluble in the polar medium used and have a molecular weight, $M_w$ (gel permeation chromatography), of from about $5 \times 10^3$ to about $5 \times 10^5$, preferably from about $1 \times 10^4$ to about $2 \times 10^5$. Nonlimiting examples include cellulose derivatives such as methyl cellulose, ethyl cellulose and hydroxypropyl cellulose, as well as polyvinyl acetate. Partially saponified polyvinyl acetates, preferably with a degree of saponification of from about 5% to about 25%, are particularly suitable. Polyvinyl pyrrolidone, substituted polyvinyl pyrrolidones, polyvinyl caprolactam and copolymers of vinyl are preferably used in quantities of from about 0.1% to about 10% by weight, preferably from about 0.2% to about 5% by weight, based on the total weight of the monomer(s) or mixtures thereof.

Other dispersing agents that may be used in the preparation of the synthetic bead polymers according to the present invention include ionic and nonionic surface active agents. Nonlimiting examples of suitable anionic surfactants are the sodium salts of sulfosuccinic acid esters. Suitable cationic surfactants include, but are not limited to, N-alkyl-ammonium salts, for example, methylcapryl ammonium chloride. Ethoxylated nonyl phenol is an example of a suitable nonionic surfactant for use. The surface active agents may be used in an amount of from about 0.1% to about 5% by weight, preferably from about 0.2% to about 2%, by weight, based on the polar medium.

Polymerization of the monomer units is initiated with conventional radical formers, in particular, peroxy compounds and azo compounds, e.g. dibenzoyl peroxide, dilauryl peroxide, bis(p-chlorobenzoylperoxide), dicyclohexylperoxidicarbonate, tert-butylperoctoate, 2,5-bis (2-ethylhexanoylperoxi)-2,5-dimethylhexane, tert-amylperoxi-2-ethylhexane, 2,2'-azo-bis(isobutyronitrile).

The polymerization temperature employed depends upon the decomposition temperature of the initiator and the boiling point of the solvent and is preferably in the range of from about 50° C. to 140° C. Polymerization is advantageously carried out at the boiling point of the solvent. The polymerization time generally extends over several hours (e.g., about 2 to 12 hours).

The polymerization mixture is usually stirred. The isolation of the polymer according to the present invention is carried out by filtration or by precipitation, for example, using a centrifuge. For the calibrator particles according to the present invention, the refractive index is determined by the monomer(s) which comprise the particles. The average particle diameter and the monodispersity (i.e., narrow distribution) are obtained using skill possessed by those in the art (e.g., U.S. Pat. No. 5,093,445), by suitably adjusting the parameters of polymerization to achieve the specific particle size and monodispersity required, based on the type(s) of calibrating/standardizing particles that are desired for flow cytometry analyses.

The determination of the refractive index as a significant characteristic of the polymer particles prepared according to the present invention can be performed as follows: a dispersion of the polymer particles was filtered and dried in an oven at about 105° C. The dried polymer was dissolved in a solvent, e.g., acetone, and a drop of the dissolved polymer solution was placed on the glass plate of a refractometer (i.e., an Abbe refractometer (see Example 3)) and was then dried (e.g., using a hair dryer) to form a continuous film over the surface of the plate. The refractive index of the particles was then measured using the refractometer on this dried polymer film.

An adjustment of the particular refractive index of the particle beads produced in accordance with the present invention can be carried out by loading the beads with a substance having a low refractive index (see Example 2). In general, in loading polymer particles, the particles are swollen, together with an organic compound (i.e., an active component), in a solvent for the polymer. After evaporation of the solvent, the active component remains within the polymer particle. Suitable loadable component compounds comprise any organic molecule with a refractive index of less than or equal to about 1.45. Examples of organic molecules suitable for loading include fluorine-containing compounds, particularly, fluorine-containing monomers as described hereinabove, which are polymerized as described directly above. To prevent the loaded substance from leaching from the beads, one or more ethylene-unsaturated monomers having a low refractive index can be added, together with a radical initiator. Subsequent polymerization immobilizes the organic molecule(s) in the particles. A description of methods used for loading particles can be found in U.S. Pat. No. 5,270,354 to J. T. Vermeersch et al.

Also encompassed by the present invention is a mixture of particles having different size and refractive index ranges, as well as different absorption and fluorescent dye concentration ranges, so that a given instrument may be calibrated/standardized using particles that are representative of all of the different types of actual blood cells that are present in a subject's blood sample.

The present invention is particularly applicable for the standardization/calibration of flow cytometry analyzer instruments involving a variety of detection mechanisms and technologies based on light scatter as but one measured parameter, for example, light scatter/absorption, light scatter/fluorescence, light scatter/electrical impedance, light scatter/radio frequency (RF), light scatter/light scatter technologies and the like. As used herein, the technologies involving flow cytometry based on scattered light combined with another measured parameter for particle and cell determination and measurement are referred to as "scatter/X" determinations. Illustratively, by scatter/scatter detection is meant that particle or cell analysis is made by measuring light scatter caused by the particles at two different scattering angles. Other systems, such as scatter/electrical impedance or scatter/RF detection allow cell analysis to be performed by measuring light scatter at at least one angle and also by measuring a different known parameter, such as electrical impedance or radio frequency, respectively.

Generally, in scatter/X methods, cells in suspension pass in single-file through an optical detection system, and also, for impedance and RF measurements, through an electrical detection system. The optical system comprises a light source, usually a collimated laser beam, a narrow cylindrical tube through which the cells pass and intercept the light beam, and one or more optical detectors, such as silicon photodiodes or photomultiplier tubes, which are arranged to collect light transmitted by, scattered by, or fluoresced from the cells. The electrical system comprises an electric field, static for electrical impedance and oscillating for RF, applied across a small opening, called an aperture, through which the cells pass. In the scatter/impedance method, for example, the flow cell may be a cylindrical aperture suitable for both optical and electrical measurements.

Accordingly, in one of its aspects, the present invention provides a method for calibrating or standardizing a flow cytometry instrument for particle analysis using substantially spherical synthetic particles as calibrators or standards. The volume and refractive index values of the calibration or standard synthetic spherical particles are predetermined so as to obtain known volume and refractive index values. The flow cytometry instrument generally provides at least one light scatter-related signal from the particles which pass through the instrument for analysis.

The volume of the synthetic spherical particles is routinely determined by employing conventional aperture impedance measurements, e.g., single channel aperture impedance, for spherical synthetic beads to obtain a known volume of the synthetic particles. Refractive index is determined by conventionally employed index matching techniques to obtain a predetermined or known refractive index value. Briefly, the index matching technique involves the preparation of a series of media or solutions having predetermined (or known) refractive index values which bracket the refractive index of the synthetic particles of interest. The particles are suspended in the medium or solution, e.g., serum albumin or sodium diatrizoate, and the suspended particles are visualized under a microscope to determine the point at which the particles "disappear" in the medium, i.e., the point at which the refractive index of the particles is most similar to that of the medium or solution.

The calibration or standardization method in accordance with the present invention generally involves passing the calibration or standard spherical synthetic particles, having average particle diameters and refractive indices essentially reproducible of particles to be assayed or analyzed, in a liquid flow stream essentially one cell at a time through an incident beam of light. A first and second measurable signal are detected from the calibration or standard synthetic particles passing through the beam of light. Either the first or the second measurable signal is light scatter. The amounts or intensities of the first and second signals are determined, thereby producing a pair of signal intensities, or a signal pair.

Using the above-described predetermined volume and refractive index values for the synthetic spherical particles, in conjunction with conventional numerical tables for converting the pair of signal intensities, for example, scattering, the pair of signal intensities is converted into volume and refractive index values to provide standardized signal-gains to the flow cytometer.

Using the standardized signal-gains, in conjunction with the aforementioned conversion tables, the flow cytometer is calibrated for volume and refractive index measurements. In addition, using the known particle concentration for the suspension of spherical particles of predetermined volume and refractive index, the flow cytometer is standardized for counting analyzable particles having signals within the appropriate volume and refractive index ranges.

It is to be understood that, in the calibrating or standardizing method in accordance with the present invention, other measurable signals, in addition to light scattering signals, can be employed. Thus, in the calibration/standardization method, either the first or the second measurable signal can be light scatter and the other of the two measurable signals can be one of those listed below. Alternatively, both the first and the second signals can be light scatter. Nonlimiting examples of suitable measurable signals, other than light scatter, that can comprise either the first or the second signal (whichever is not light scatter), or that can be employed as signals in addition to light scatter, include electrical impedance, light absorption, fluorescence and radio frequency, in any combination. As an example, in the case where either the first or the second measurable signal is light scatter, and the other non-light scattering signal is another kind of meaurable signal, the measured signals are used to provide volume and refractive index measurements.

If both the first and the second measurable signals are light scatter, then the other measurable signals, used in addition to the light scattering signals, can provide additional useful determinations or measurements for the calibration/standardization method according to the present invention. As a nonlimiting example, if a fluorescence measurement is added to the first and second light scattering measurements, then a determination of fluorescence intensity can be provided, in addition to the scattering measurements obtained from the two scattering angles. As another example, if an absorbance measurement is added to the first and second light scattering measurements, then a determination of the amount of light absorbed, for example, by certain dyes within the particles being analyzed, is provided in addition to the scattering measurement obtained from the two scattering angles.

In a typical scatter/impedance analysis, an aliquot of whole blood containing red blood cells, white blood cells and platelets is diluted and suspended in an isotonic medium (which is therefore electrically conductive). The dilution factor is adjusted so that cells pass in single file through the dual detection system. The impedance measurement provides cell-size information for all of the cell types (i.e., red cells, white cells and platelets) in the whole blood sample aliquot. The scattering measurement can provide information about cell refractive index, and therefore, cell density, for cells that behave as spheres, since the Mie Scattering Theory may be applied to the scattering signal to determine refractive index. The size and/or refractive index information is used to assign signals to the three cell types. The number of pulses of each type is used to determine the cell counts.

To standardize and calibrate a scatter/X method for red blood cell analysis, spherical beads whose average volume is equivalent to that of normal red blood cells (approximately 90 fl), i.e., beads having average diameters of approximately 5.5 $\mu$m and whose average refractive index is equivalent to that of normal red blood cells (approximately 1.41), are prepared and used according to the present invention. Suspensions of known concentrations of these beads are prepared and run through the scatter/X detection system. The scatter/X signals generated by these beads are used to standardize the detectors for red blood cell measurements, since the standardizing beads determine the signal positions occupied by normal cell populations.

The volume and refractive index values of the beads can also be used to calibrate the detection system for numerical measurements, such as mean red blood cell volume (MCV) and mean cellular hemoglobin concentration (MCHC). The latter parameter is obtainable from refractive index measurements, since refractive index and hemoglobin concentration are linearly related. The number of signals generated by the beads per unit time or per unit volume can be used to calibrate the system for red blood cell counts (RBC).

In an entirely analogous manner, synthetic beads in accordance with the invention can be prepared and employed for standardizing and calibrating an instrument for performing platelet analyses. Spherical particles of approximately 2.5 $\mu$m diameter and approximately 1.38 refractive index in a suspension of appropriate dilution are run through the system. The signals of the particles are used to standardize the detection system for platelet measurements. The particles' signals can also be used to calibrate the system for mean platelet volume (MPV) measurements, as well as for platelet refractive index measurements. The number of signals per unit time or per unit volume can be used to calibrate platelet counts (PLT).

In an analogous manner, synthetic particles in accordance with the present invention can be prepared and selected for use in standardizing and calibrating instruments for white blood cell analyses. In this instance, a single set of particles having, for example, an average diameter of about 8.0 $\mu$m and a refractive index of about 1.385, and appropriately diluted, can be prepared and selected for standardizing and calibrating the detection system for white blood cell analyses, in general. Alternatively, multiple sets of particles having selected average diameters, refractive indices and concentrations, may be used separately or in combination to standardize and calibrate the detection system for white blood cell analyses on a white blood cell type-by-type basis.

As described for white blood cell analyses, rather than individually standardizing and calibrating a system for the analysis of each blood cell type, a combination of beads suitable for the simultaneous analysis of red blood cells, platelets and each white blood cell type can be prepared in a single suspension of appropriate concentration. This is possible because, for normal blood samples, all of the blood cell types occupy unique positions in size/refractive index space.

In addition, particles in accordance with the present invention can be prepared and selected for standardizing and calibrating instruments for the analysis of reticulocytes in whole blood. Similar to those for standardizing/calibrating red blood cells, the particles for reticulocyte standardization/calibration have diameters of about 5.5 $\mu$m and refractive indices of about 1.41. If the reticulocytes are distinguished from mature red blood cells based on the optical absorption characteristics of selectively bound dyes, e.g., cationic dyes, such as Oxazine 750, then the particles are prepared to contain dyes at concentrations that are representative of those of reticulocytes. If the reticulocytes are distinguished from red blood cells on the basis of the fluorescence of selectively bound dyes, then the beads contain suitable fluorescent dyes, as are commonly known to and employed by the skilled practitioner. The preparation of the polymer particles to contain suitable dye compounds can be achieved in a manner analogous to that described for loading the particles with fluorine-containing compounds, as described above in the Detailed Description and in Example 2. Instead of loading the particles with F-containing compounds, the particles can be loaded with pigment compounds or hydrophobic dyes, for example (see also U.S. Pat. No. 5,270,354).

Figure 1B:
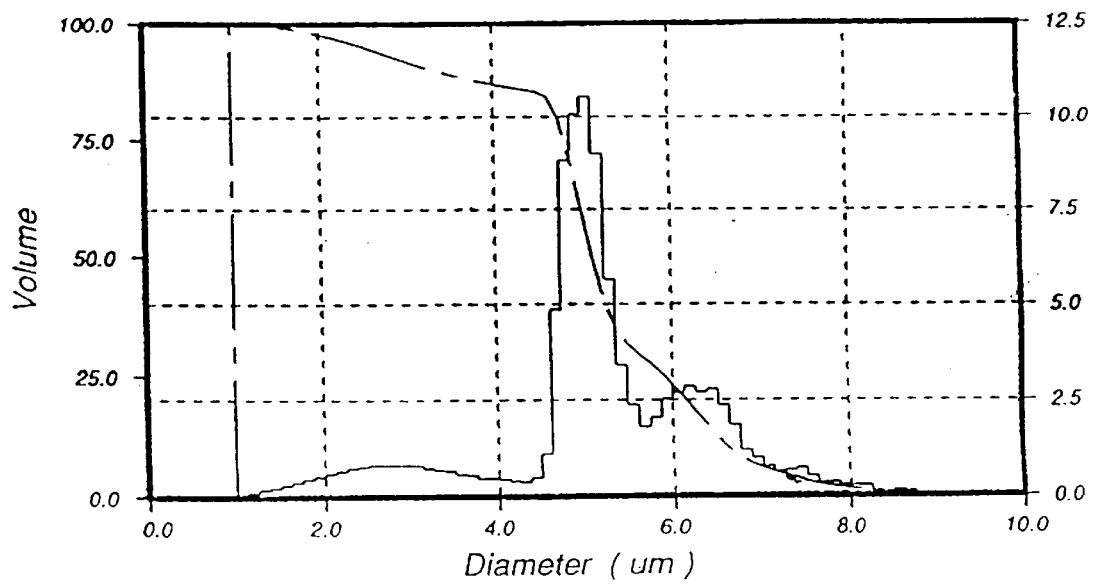

To employ the spherical particles prepared in accordance with the present invention as standards/calibrators in flow cytometry, the size and refractive index values of the particles must be determined. Size may be determined based on previously-calibrated aperture impedance counters by simply running the particles through the counters and recording their volumes (FIGS. 1A and 1B).

Further to the above-described refractive index measurement of the particles, refractive index values may be determined by a form of refractive index matching, as discussed above and further described herein: Beads are suspended in a series of fluid media whose refractive indices span the refractive index value of the polymer particle beads. The suspension is observed under a microscope. The bead refractive index is the value at which the beads are microscopically invisible (since their refractive index "matches" that of the medium). The refractive index of the medium can be determined by measurements on an Abbe refractometer, for example. The medium selected must be immiscible with the beads. Otherwise, the beads will absorb some of the medium and this will affect their refractive index values. Suitable media include, but are not limited to, aqueous solutions of sugars, such as dextran. The refractive index resolution is controlled by the resolution of refractive index increments of the prepared media solution. Practically, the refractive index may be incremented by as little as 0.0005 units.

The Abbe refractometer allows refractometric analysis using but a drop or two of sample and allowing a measurement of refractive index to be made in about 1–2 minutes with a precision of 0.0001 (*McGraw-Hill Concise Encyclopedia of Science and Technology*, Second Edition, Editor-in-chief: Sybil P. Parker, McGraw-Hill Publishing Company, p. 1582, 1989).

EXAMPLES

The following examples as set forth herein are meant to exemplify the various aspects of carrying out the invention and are not intended to limit the invention in any way.

EXAMPLE 1
Preparation of Fluorinated Polymer Particle Beads with a Particle Size Diameter of about 5 $\mu$m and a Refractive Index of 1.41+/−0.01

Synthetic particles were prepared for use as calibration standards for red blood cells. The particles were homopolymers comprised of polymerized monomeric units of trifluoroethylmethacrylate as monomer. The procedure used to produce the particles is described in Example 1.

At room temperature, 6.64 g of poly-N-vinyl pyrrolidine having a molecular weight of 40,000 was dissolved together with 665.0 g of trifluoroethylmethacrylate and 13.3 g ArkopalN060 (see below) in 33.69 g of demineralized water and 2670.53 g of methanol in a 5 liter reaction vessel equipped with a stirrer and a reflux condenser. The solution was stirred constantly at 55 rpm during the entire reaction. The reaction mixture was heated to 65° C. At this temperature, 110.83 g of a 30%, w/w, solution of sodium persulfate was added at once. The reaction mixture was held at 65° C. and was stirred for another 16 hours. The reaction mixture was allowed to cool to room temperature and was filtered. The final diameter size of the particles (Dmv) was 5.13 and the refractive index was 1.413. Fluorine was present in an amount of 35%, by weight, with respect to the monomers, in the final particles comprising polymerized fluorine-containing monomers in accordance with the present invention.

Polyvinyl pyrrolidone (PVP) used in the above-described preparation of the fluorinated polymer beads serves as a stabilizing agent. PVP is advantageous for the monodispersity of the particles. Also, because it is nontoxic, it is a good binding agent for medical applications. Arkopal N-060, a mono-isononylphenyl ether of a polyethylene glycol with recurring ethyleneoxide units, is an example of a wetting agent. Examples of other suitable wetting agents include Akyporox NP-40, a mono-isononylphenyl ether of a polyethylene glycol with four recurring ethyleneoxide units and Antarox CO-630, a mono-isononylphenyl ether of a polyethylene glycol with nine to ten recurring ethyleneoxide units.

EXAMPLE 2
Loading Synthetic Polymer Particles to Achieve Calibration Materials Having A Low Refractive Index Synthetic polymer particles were prepared in accordance with the present invention and were loaded to adjust the refractive index to achieve calibration products having low refractive indices without leaching of the loaded material.

2 g of perfluoroalkylethylmethacrylate was dissolved in 45 ml ethylacetate at 25° C. The resulting solution was dispersed for 5 minutes with stirring at 12,000 rpm in 90 ml of demineralized water to which 9 ml of a 10% aqueous solution of the sodium salt of n-dodecylbenezene sulfonic acid had been added. The resulting dispersion of perfluoromonomer was added to 97 g of an aqueous dispersion of fluor beads (20.6%, w/w; refractive index: 1.413). The mixture obtained was stirred for 1 hour. Ethylacetate was removed under reduced pressure. Homodisperse polymer particles loaded with the hydrophobic perfluoromonomer (refractive index: 1.408) were obtained. The dispersion did not contain conglomerates or undissolved or crystallized perfluoromonomer.

EXAMPLE 3
Standardization and Calibration of Bayer H*1 Hematology Analyzer using the Synthetic Polymer Particles of the Present Invention Prior to the Analysis of Cell Populations in Whole Blood Synthetic beads were prepared according to the method described in Example 1 above. The beads were then dried at 50° C. and were resuspended in isotonic saline to a final concentration of 23,500 particles per $\mu$l of saline. Based on the particle count and size distribution provided by the aperture impedance counter (FIGS. 1A and 1B), the bead suspension comprised 7,888 particles having an average particle diameter of 4.89+/−0.17 $\mu$m and 15,612 particles having an average particle diameter of less than 2.0 $\mu$m. The average refractive index of these beads was 1.417+/−0.003.

Figure 2:
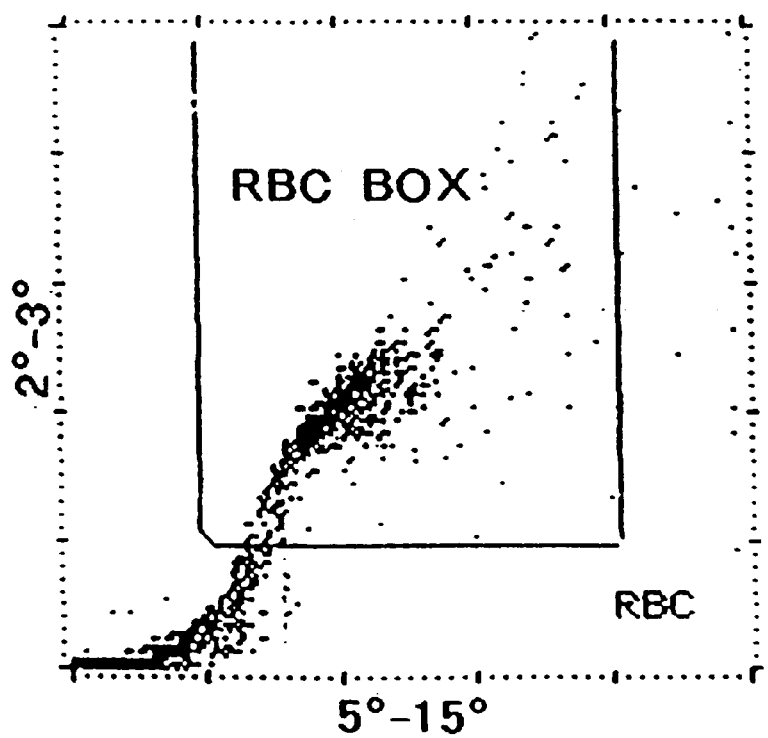
FIG. 2 shows a scatter/scatter cytogram for the same particles as described in FIGS. 1A and 1B. The X-axis represents the scattering intensity of the particles at 5°–15° and the Y-axis represents the scattering intensity of the particles at 2°–3°. The X- and Y-axis values range from 0 to 50. In addition to the cytogram, the mean and standard deviation (SD), called Sigmax and Sigmay, of the distribution of the particles in the RBC box are presented. The particle count, called RBC ($10^6/\mu l$); the mean particle volume, called MCV (fl); the mean refractive index, mathematically transformed into an equivalent cellular hemoglobin concentration mean, CHCM (g/dl), as described herein; and the volume and hemoglobin concentration distribution widths, called RDW (%) and HDW (SD), respectively, are shown (see Example 3).

Samples of this bead suspension were run on the Bayer H*1 Hematology Analyzer in Direct Cytometry mode; that is, the suspension was not further diluted before passing through the scatter/scatter optical detection system. This was done to reduce the consumption of the standardization/ calibration particle material. The scatter/scatter system of the Bayer H*1 instrument contains a Helium-Neon laser light source emitting at a wavelength of 632.8 nanometers; a cylindrical aperture through which the suspension passed (the aperture is sheathed in a medium whose refractive index matched that of the suspending medium); and two silicon photodetectors, one placed to collect the light scattered by the particles from 2°–3°, and the other placed to collect the light scattered from 5°–15°. The signals were displayed on a direct scatter/scatter cytogram, in which the X-axis signal corresponds to the 5°–15° scatter and the Y-axis signal corresponds to the 2°–3° scatter (FIG. 2). The particle size was presented as mean cell volume (MCV, fl) to correspond to the relevant term for authentic red blood cells. Similarly, the size distribution was presented as the red blood cell distribution width (RDW, %, (SD of red blood cell distribution/MCV)). MCV is related to diameter as follows:

$$MCV = \pi \times diameter^3/6.$$

The refractive index was presented as the cellular hemoglobin concentration mean (CHCM, g/dl) and its distribution was presented as the hemoglobin distribution width (HDW, g/dl, (SD of the distribution)). Cellular hemoglobin concentration (HC) is related to refractive index as follows: HC =(cellular refractive index−1.345)/0.001942, where 1.345= the refractive index of the non-hemoglobin portion in red blood cell cytoplasm and 0.001942=refractive index increment per g/dl of hemoglobin.

The associated scattering signal values (designated as Meanx and Meany in FIG. 2) were determined using tables based on Mie Scattering Theory, which predicts the angular scattering intensity pattern for homogeneous spheres as a function of incident wavelength, particle refractive index and particle diameter. The values were adjusted until they agreed with the theoretical prediction: X=19.5 and Y=20.0. The particle count for beads within the red blood cell "box" in FIG. 2 is 625 times higher than the actual count (i.e., 7,888×625=4,930,000). This includes the system's normal dilution factor of 625/1.

The contents of all patents, patent applications, published articles, books, references, manuals, and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description or defined in the appended claims be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A method for calibrating or standardizing a flow cytometry instrument for particle analysis using substantially spherical synthetic particles as calibrators or standards, said calibration or standard synthetic particles having predetermined volume and refractive index values, wherein said instrument provides at least one light scatter-related signal from particles passing through said instrument for analysis, comprising:
   a) passing said calibration or standard synthetic particles having average particle diameters and refractive indices essentially reproducible of particles to be assayed in a liquid flow stream essentially one cell at a time through an incident beam of light;
   b) detecting a first and a second measurable signal from said calibration or standard synthetic particles passing through said beam of light;
   c) determining the intensities of said first and second signals, thereby producing a pair of signal intensities;
   d) converting said pair of signal intensities into volume and refractive index values to provide standardized signal-gains to the flow cytometer; and
   e) calibrating the flow cytometer for i) volume and refractive index measurements and for ii) counting analyzable particles having signals within appropriate volume and refractive index ranges.

2. The method according to claim 1, wherein the converting step d) is performed using predetermined volume and refractive index values of the synthetic spherical particles in conjunction with numerical conversion tables.

3. The method according to claim 1, wherein said calibrating step e) i) is performed using standardized signal-gains in conjunction with numerical conversion tables.

4. The method according to claim 1, wherein said calibrating step e) ii) is performed using predetermined particle concentration of a suspension of spherical synthetic particles of predetermined volume and refractive index.

5. The method according to claim 1, wherein either said first or said second measurable signal comprises light scatter and the other of said first or said second measurable signal comprises at least one of light scatter, electrical impedance, light absorption, fluorescence or radio frequency.

6. The method according to claim 1, wherein additional measurable signals are obtained, said additional signals comprising, in any combination, one or more of light scatter, electrical impedance, light absorption, fluorescence or radio frequency.

7. The method according to claim 1, wherein said average particle diameter of said calibration particles is from about 1 μm to about 8 μm.

8. The method according to claim 7, wherein said average particle diameter of said calibration particles is from about 4 μm to about 6 μm.

9. The method according to claim 1, wherein said refractive index of said calibration particles is from about 1.35 to about 1.45.

10. The method according to claim 9, wherein said refractive index of said calibration particles is from about 1.40 to about 1.42.

11. The method according to claim 1, further wherein said calibration or standard synthetic particles have a particle size distribution width of from about 1% to about 5%.

12. The method according to claim 1, wherein said synthetic particles have a monodispersity of at least about 60% to about 85%.

13. The method according to claim 1, wherein said calibration particles comprise polymerized monomers of the formulae selected from the group consisting of:

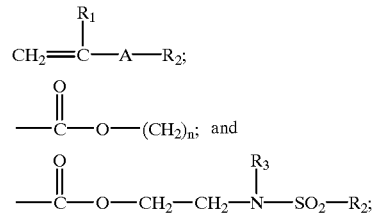

wherein, $R_1$ is hydrogen (H) or methyl ($CH_3$); A is —O—; n is about 1–5; $R_2$ is a fluorine-containing alkyl group of 1 to 12 carbon atoms, said alkyl group selected from the group consisting of perfluoralkyls and partially fluorinated alkyls; and $R_3$ is H or $C_1$–$C_6$ alkyl.

14. The method according to claim 13, wherein said monomers comprise 2-fluorethylacrylate, 2,2,2-trifluoroethylacrylate, 2,2,3,3-tetrafluoropropylacrylate, 2,2,3,4,4,4-hexafluorobutylacrylate, 1H,1H-heptafluorobutylacrylate, 1H,1H,5H-octafluoropentylacrylate, 1H,1H-pentadecafluoroctylacrylate, 2-fluoroethylmethacrylate, 2,2,2-trifluoroethylmethacrylate, 2,2,3,3,3-pentafluoropropylmethacrylate, 1H,1H-hepatafluorobutylmethacrylate, 2,2,3,4,4,4-hexafluorobutylmethacrylate, 1H1H,5H-octafluoropentylmethacrylate, 1H,1H,11H-eicosafluoroundecylmethacrylate and mixtures thereof.

15. The method according to claim 1, wherein said calibration particles have the formula:

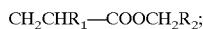

$$CH_2CHR_1\text{—}COOCH_2R_2;$$

wherein $R_1$ is hydrogen or methyl and $R_2$ is a fluorine-containing alkyl group having 1 to 12 carbon atoms, said alkyl group being selected from the group consisting of perfluoralkyls and partially fluorinated alkyls.

16. The method according to claim 1, wherein said calibration or standardization is performed on a hematology analyzer.

17. The method according to claim 16, wherein said particles to be analyzed are blood cells.

18. The method according to claim 17, wherein said blood cells are selected from the group consisting of erythrocytes, reticulocytes, white blood cells and platelets.

19. A method for calibrating or standardizing a flow cytometry instrument for particle analysis using substantially spherical synthetic particles as calibrators or standards, said calibration or standard synthetic particles having predetermined volume and refractive index values, wherein said instrument provides at least one light scatter-related signal from particles passing through said instrument for analysis, comprising:

a) passing said calibration or standard synthetic particles, having average particle diameters and refractive indices essentially reproducible of particles to be assayed in a liquid flow stream, essentially one cell at a time through an incident beam of light;

b) detecting a first measurable light scatter signal from said calibration or standard synthetic particles passing through said beam of light;

c) detecting a second measurable signal from said calibration or standard synthetic particles;

d) determining the intensity of said first light scatter signal and said second signal, thereby producing a pair of signal intensities;

e) converting said pair of signal intensities into volume and refractive index values over a range of pairs of signals to provide standardized signal-gains to the flow cytometer; and f) calibrating the flow cytometer for i) volume and refractive index measurements and for ii) counting analyzable particles having signals within appropriate volume and refractive index ranges.

20. The method according to claim 19, wherein said converting step e) is performed using predetermined volume and refractive index values of the synthetic spherical particles in conjunction with numerical conversion tables.

21. The method according to claim 19, wherein said calibrating step f) i) is performed using standardized signal-gains in conjunction with numerical conversion tables.

22. The method according to claim 19, wherein said calibrating step f) ii) is performed using predetermined particle concentration of a suspension of spherical synthetic particles of predetermined volume and refractive index.

23. The method according to claim 19, wherein said second measurable signal comprises light scatter, electrical impedance, light absorption, fluorescence, or radio frequency.

24. A method for calibrating or standardizing a flow cytometry instrument for particle analysis using substantially spherical synthetic particles as calibrators or standards, said calibration or standard synthetic particles having characteristic and known volume and refractive index values, wherein said instrument provides at least one light scatter-related signal from particles passing through said instrument for analysis, comprising:

a) passing said calibration or standard synthetic particles, having average particle diameters and refractive indices essentially reproducible of particles to be assayed in a liquid flow stream, essentially one cell at a time through an incident beam of light;

b) detecting first and second measurable light scatter signals from said calibration or standard synthetic particles passing through said beam of light;

c) determining the intensities of said first and second light scatter signals, thereby producing a pair of signal scattering intensities;

d) converting said pair of signal scattering intensities into volume and refractive index values over a range of pairs of signals to provide standardized signal-gains to the flow cytometer; and e) calibrating the flow cytometer for i) volume and refractive index measurements and for ii) counting analyzable particles having signals within appropriate volume and refractive index ranges.

25. The method according to claim 24, wherein said converting step d) is performed using predetermined volume and refractive index values of the synthetic spherical particles in conjunction with numerical conversion tables.

26. The method according to claim 24, wherein said calibrating step e) i) is performed using standardized signal-gains in conjunction with numerical conversion tables.

27. The method according to claim 24, wherein said calibrating step e) ii) is performed using a predetermined particle concentration of a suspension of spherical synthetic particles of predetermined volume and refractive index.

28. The method according to claim 24, wherein additional measurable signals are obtained and comprise electrical impedance, light absorption, fluorescence radio frequency, or combinations thereof.

* * * * *